United States Patent
Zhu

(10) Patent No.: US 12,403,206 B2
(45) Date of Patent: Sep. 2, 2025

(54) HIGH-ADAPTABILITY PULSED ULTRAVIOLET DISINFECTION AND STERILIZATION SYSTEM

(71) Applicant: BEIJING ZHONGKE CHANGJIAN ENVIRONMENTAL TREATMENT TECHNOLOGY CO., LTD., Beijing (CN)

(72) Inventor: Jincai Zhu, Beijing (CN)

(73) Assignee: BEIJING ZHONGKE CHANGJIAN ENVIRONMENTAL TREATMENT TECHNOLOGY CO., LTD., Beijing (CN)

(*) Notice: Subject to any disclaimer, the term of this patent is extended or adjusted under 35 U.S.C. 154(b) by 114 days.

(21) Appl. No.: 18/551,775

(22) PCT Filed: Jun. 13, 2022

(86) PCT No.: PCT/CN2022/098470
§ 371 (c)(1),
(2) Date: Sep. 21, 2023

(87) PCT Pub. No.: WO2022/267924
PCT Pub. Date: Dec. 29, 2022

(65) Prior Publication Data
US 2024/0173447 A1    May 30, 2024

(30) Foreign Application Priority Data

Jun. 25, 2021 (CN) .......................... 202110714692.6
Oct. 28, 2021 (CN) .......................... 202122619392.8
(Continued)

(51) Int. Cl.
*A61L 2/10* (2006.01)
*A61L 2/24* (2006.01)

(52) U.S. Cl.
CPC .................. *A61L 2/10* (2013.01); *A61L 2/24* (2013.01); *A61L 2202/11* (2013.01); *A61L 2202/122* (2013.01); *A61L 2202/14* (2013.01)

(58) Field of Classification Search
CPC .......... A61L 2/10; A61L 2/24; A61L 2202/11; A61L 2202/122; A61L 2202/14
See application file for complete search history.

(56) References Cited

U.S. PATENT DOCUMENTS 12,263,260 B1 * 4/2025 Whitaker .................. A61L 2/24
2017/0157276 A1 * 6/2017 Dobrinsky ................ A61L 2/24
(Continued)

FOREIGN PATENT DOCUMENTS

| AU | 2020102582 A4 | 11/2020 |
|----|---------------|---------|
| CN | 109393300 A | 3/2019 |

(Continued)

OTHER PUBLICATIONS

Translation of IDS Doc CN109393300 (Year: 2019).*
Translation of IDS Doc CN112061676 (Year: 2020).*
Translation of IDS Doc CN112656971(Year: 2021).*

*Primary Examiner* — Drew A Dunn
(74) *Attorney, Agent, or Firm* — Justin Lampel

(57) ABSTRACT

The disclosure relates to a high-adaptability pulsed ultraviolet disinfection and sterilization system. The system includes: a channel-type ultraviolet disinfection and sterilization device, including a device body, a conveyor and a first pulsed ultraviolet disinfection and sterilization apparatus, two ends of the device body being respectively provided with an item inlet and an item outlet; a handheld ultraviolet disinfection and sterilization device, including a handheld shell, a lamp holder and a second pulsed ultraviolet disinfection and sterilization apparatus, a periphery of the handheld shell being provided with a control switch, an inner wall of the handheld shell being provided with a single-chip (Continued)

microcomputer, and one end of the single-chip microcomputer being electrically connected to the second pulsed ultraviolet disinfection and sterilization apparatus and the control switch; and an ultraviolet disinfection and sterilization cabinet, including a casing and a third pulsed ultraviolet disinfection and sterilization apparatus, the third pulsed ultraviolet disinfection and sterilization apparatus being connected to the casing. Thereby, in order to solve the problems of single function, limited disinfected and sterilized positions and limited applicable objects in the ultraviolet disinfection cabinet in the prior art, it is necessary to provide a more reasonable technical solution to disinfect and sterilize different items in different states under different conditions.

10 Claims, 4 Drawing Sheets

(30) Foreign Application Priority Data

Feb. 25, 2022 (CN) .......................... 202220405043.8
Feb. 25, 2022 (CN) .......................... 202220405045.7

(56) References Cited

U.S. PATENT DOCUMENTS

| | | | |
|---|---|---|---|
| 2018/0117194 A1* | 5/2018 | Dobrinsky | G01N 21/6486 |
| 2018/0207303 A1* | 7/2018 | Farren | A61L 2/10 |
| 2020/0360549 A1* | 11/2020 | Neveu | A61L 2/26 |
| 2022/0305159 A1* | 9/2022 | Collet | A61L 2/10 |

FOREIGN PATENT DOCUMENTS

| | | |
|---|---|---|
| CN | 209204139 U | 8/2019 |
| CN | 111330038 A | 6/2020 |
| CN | 211485795 U | 9/2020 |
| CN | 111905123 A | 11/2020 |
| CN | 111920977 A | 11/2020 |
| CN | 111939281 A | 11/2020 |
| CN | 112061676 A | 12/2020 |
| CN | 112656971 A | 4/2021 |
| JP | 2005312978 A | 11/2005 |

* cited by examiner

HIGH-ADAPTABILITY PULSED ULTRAVIOLET DISINFECTION AND STERILIZATION SYSTEM

FIELD OF TECHNOLOGY

The disclosure relates to the technical field of item disinfection and sterilization devices, particularly to a high-adaptability pulsed ultraviolet disinfection and sterilization system.

BACKGROUND

The traditional methods for disinfecting and sterilizing items usually use chemicals or a low-pressure mercury lamp. These methods may cause residues of harmful substances and degradation of quality of items, causing adverse effects on the disinfected items. With the popularity of ultraviolet sterilization and disinfection technology, such problems have been improved.

The ultraviolet sterilization and disinfection can destroy the molecular structure of DNA (deoxyribonucleic acid) or RNA (ribonucleic acid) in microbial cells by using ultraviolet light with appropriate wavelength, and can achieve growth cell death and/or regenerative cell death, thus achieving the effects of sterilization and disinfection.

To this end, disinfection cabinets came into being. A disinfection cabinet is a tool that can dry, sterilize, disinfect, thermally insulate and dehumidify utensils, tableware, towels, clothes, hairdressing and beauty supplies, and medical appliances by using ultraviolet light, far-infrared light, high temperature and ozone. However, ultraviolet disinfection cabinets usually kill bacteria by emitting ultraviolet light to the surface of items to be disinfected through an ultraviolet lamp. In the prior art, in most of the disinfection cabinets, positions of the ultraviolet lamp and the item to be disinfected are relatively fixed, and the ultraviolet light is emitted to a fixed position on the item to be disinfected. Thus, the item to be disinfected may be irradiated unevenly, and there may be positions that cannot be irradiated, resulting in incomplete sterilization and poor sterilization effect. Moreover, the long working time of the ultraviolet lamp will cause rising temperature, affecting its service life.

Therefore, the ultraviolet disinfection cabinet in the prior art can only sterilize limited positions of the item, thus having narrow applicability. In addition, based on the characteristics of the ultraviolet disinfection cabinet, the ultraviolet disinfection cabinet is not applicable to moving items, making it applicable to limited objects. Furthermore, for a single item that needs to be sterilized separately, although the ultraviolet disinfection cabinet can disinfect and sterilize this item, it consumes a lot of energy and is less economical and inefficient.

In view of the problems of single function, limited disinfected and sterilized positions and limited applicable objects in the ultraviolet disinfection cabinet in the prior art, it is necessary to provide a more reasonable technical solution to disinfect and sterilize different items in different states under different conditions.

SUMMARY

An objective of the disclosure is to provide a high-adaptability pulsed ultraviolet disinfection and sterilization system, to solve the problems of single function, limited disinfected and sterilized positions and limited applicable objects in the ultraviolet disinfection cabinet in the prior art.

In order to achieve the above objective, the disclosure provides a high-adaptability pulsed ultraviolet disinfection and sterilization system, including a channel-type ultraviolet disinfection and sterilization device for disinfecting and sterilizing moving items, a handheld ultraviolet disinfection and sterilization device for randomly disinfecting and sterilizing relatively static items, and an ultraviolet disinfection and sterilization cabinet for disinfecting and sterilizing static items.

The channel-type ultraviolet disinfection and sterilization device includes a device body, a conveyor and a first pulsed ultraviolet disinfection and sterilization apparatus. Two ends of the device body are respectively provided with an item inlet and an item outlet. The item inlet communicates with the item outlet to form a disinfection and sterilization channel. The item inlet and the item outlet are respectively provided with a roller shutter door for opening or closing the disinfection and sterilization channel in one-to-one correspondence. The conveyor is configured to carry and convey items such that the items are conveyed from the item inlet to the item outlet. An inner wall of the disinfection and sterilization channel is provided with the first pulsed ultraviolet disinfection and sterilization apparatus so as to disinfect and sterilize the items conveyed on the conveyor.

The handheld ultraviolet disinfection and sterilization device includes a handheld shell, a lamp holder and a second pulsed ultraviolet disinfection and sterilization apparatus. The second pulsed ultraviolet disinfection and sterilization apparatus is connected to the handheld shell through the lamp holder. A periphery of the handheld shell is provided with a control switch, and an inner wall of the handheld shell is provided with a single-chip microcomputer. One end of the single-chip microcomputer is electrically connected to the second pulsed ultraviolet disinfection and sterilization apparatus, and the other end of the single-chip microcomputer is electrically connected to the control switch.

The ultraviolet disinfection and sterilization cabinet includes a casing and a third pulsed ultraviolet disinfection and sterilization apparatus. The casing is provided with an inner cavity for accommodating items. A middle part of the inner cavity is provided with a transparent divider. A turntable and a guide rail ring are arranged inside the transparent divider. A transparent carrying plate is embedded in the turntable. The transparent carrying plate extends to a top surface of the transparent divider. A bottom of the transparent divider is provided with a first motor. The first motor is configured to drive the turntable to rotate on the guide rail ring. The third pulsed ultraviolet disinfection and sterilization apparatus is connected to the casing so as to disinfect and sterilize the items in the inner cavity.

In a possible design, the first pulsed ultraviolet disinfection and sterilization apparatus, the second pulsed ultraviolet disinfection and sterilization apparatus and the third pulsed ultraviolet disinfection and sterilization apparatus are configured as disinfection and sterilization apparatuses having same components. The disinfection and sterilization apparatus includes a photoelectric main module, an auxiliary function options module and an automatic control module.

The photoelectric main module includes a high-energy driving power supply and a pulsed xenon light source. The auxiliary function options module includes a water/air-cooling heat dissipation module, a cold light source filtering module and a photocatalytic module. The high-energy driving power supply is connected to the pulsed xenon light source through the automatic control module, and the water/air-cooling heat dissipation module, the cold light source filtering module and the photocatalytic module are all connected to the automatic control module.

In a possible design, the pulsed xenon light source is formed by performing high-strength sealing on a high-pressure-resistant lamp tube filled with high-pressure xenon at a high temperature of 600° ° C. to 1200° C., and the automatic control module is connected to the high-energy driving power supply in a telecommunication manner so as to adjust UVC band energy excited by one pulse of the pulsed xenon light source.

In a possible design, the photoelectric main module is configured to be capable of working stably within a temperature range of −60° ° C. to 60° C., and the photoelectric main module is capable of exciting ultraviolet light within a band of 200 nm to 280 nm.

In a possible design, there are three first pulsed ultraviolet disinfection and sterilization apparatuses respectively arranged on the inner wall of the disinfection and sterilization channel so as to generate pulsed ultraviolet light to disinfect and sterilize the items to be disinfected on the conveyor from all directions.

In a possible design, a first controller is arranged in the device body, and a periphery of the device body is provided with a touch panel. The first controller is communicatively connected to the touch panel, the conveyor and the first pulsed ultraviolet disinfection and sterilization apparatus.

A power module is arranged in the device body, and the power module is respectively electrically connected to the first controller, the touch panel, the conveyor and the first pulsed ultraviolet disinfection and sterilization apparatus so as to supply power thereto.

The conveyor includes a support, a conveyor belt and an electric motor. The conveyor belt is mounted on the support, and the electric motor is configured to drive and control the conveyor belt to operate and communicatively connected to the first controller.

In a possible design, a water chiller is arranged in the device body, and a first cooling water tube is arranged in a protective shell of the first pulsed ultraviolet disinfection and sterilization apparatus. The first cooling water tube communicates with the water chiller, and the water chiller is communicatively connected to the first controller. Cooling water is injected into an internal circulation of the first cooling water tube by the water chiller so as to cool and protect the first pulsed ultraviolet disinfection and sterilization apparatus.

A temperature sensor for detecting a temperature of water is arranged in the water chiller, and the temperature sensor is electrically connected to the first controller.

In a possible design, an alarm is arranged in the device body. The alarm is electrically connected to the first controller.

An ultraviolet sensor is arranged in the disinfection and sterilization channel. The ultraviolet sensor is electrically connected to the first controller.

In a possible design, a second cooling water tube runs through the lamp holder, and the handheld shell is provided with a grip. The grip having a hollow structure inside. The grip is provided with a tube hole, and the second cooling water tube runs through the grip and extends to a water tank outside the grip through the tube hole.

In a possible design, the handheld shell is provided with a disinfection and sterilization window arranged corresponding to the second pulsed ultraviolet disinfection and sterilization apparatus, and the disinfection and sterilization window is made of a transparent material.

By means of the above technical solution, one or more of the channel-type ultraviolet disinfection and sterilization device, the handheld ultraviolet disinfection and sterilization device and the ultraviolet disinfection and sterilization cabinet can be selected according to the object to be sterilized. On the one hand, an appropriate disinfection and sterilization device can be selected according to the state of the item to disinfect and sterilize the item in all directions, such that the item can be disinfected and sterilized thoroughly. On the other hand, the energy consumption can be reduced, and the disinfection and sterilization efficiency can be improved. As a result, no matter whether the items are dynamic or static or how many items are to be disinfected and sterilized, they can be effectively disinfected and sterilized by the high-adaptability pulsed ultraviolet disinfection and sterilization system, thereby ensuring food sanitation and living sanitation and preventing bacteria from affecting human health and safety.

Other features and advantages of the disclosure will be described in detail in the detailed description which follows.

BRIEF DESCRIPTION OF THE DRAWINGS

The accompanying drawings are provided to provide a further understanding of the disclosure and constitute a part of the specification. They are used to explain the disclosure together with the specific implementations below, but are not intended to limit the disclosure. In the accompanying drawings.

DESCRIPTION OF REFERENCE SIGNS

Figure 1:
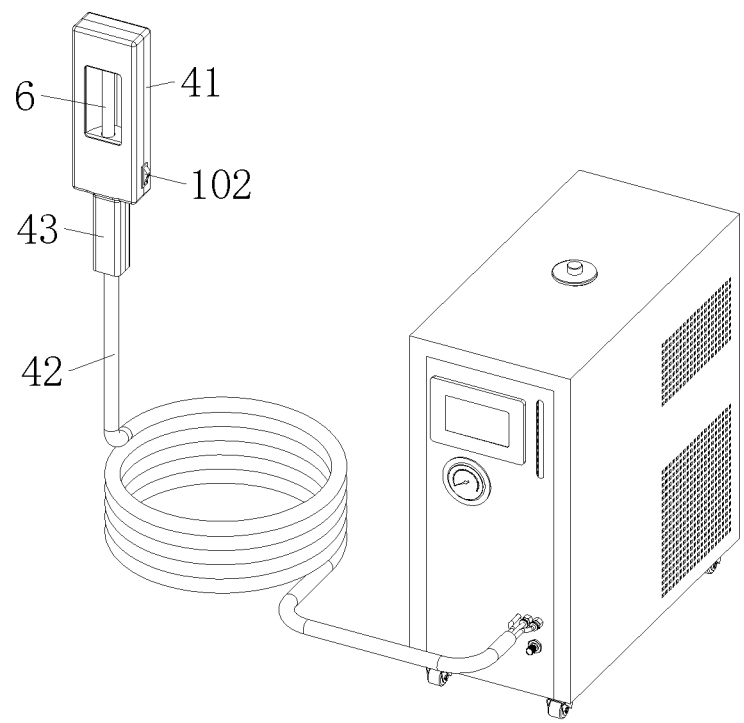
FIG. 1 is a schematic three-dimensional structural view of a handheld ultraviolet disinfection and sterilization device in a high-adaptability pulsed ultraviolet disinfection and sterilization system according to an embodiment.

1—device body, 11—item inlet, 12—item outlet, 13—window shade, 14—touch panel, 15—first controller, 2—conveyor, 3—first pulsed ultraviolet disinfection and sterilization apparatus, 41—handheld shell, 42—second cooling water tube, 43—grip, 44—disinfection and sterilization window, 45—heat dissipation through hole, 5—lamp holder, 6—second pulsed ultraviolet disinfection and sterilization apparatus, 71—casing, 72—first motor, 73—turntable, 74—guide rail ring, 75—transparent carrying plate, 76—heat dissipation fan, 77—heat dissipation shutter, 8—third pulsed ultraviolet disinfection and sterilization apparatus, 91—first water chiller, 92—power module, 101—single-chip microcomputer, 102—control switch.

DESCRIPTION OF THE EMBODIMENTS

Specific implementations of the disclosure will be described in detail below in conjunction with the accompanying drawings.

According to specific implementations of the disclosure, a high-adaptability pulsed ultraviolet disinfection and sterilization system is provided. FIG. 1 to FIG. 8 show one of the specific implementation.

Referring to FIG. 1 to FIG. 8, the high-adaptability pulsed ultraviolet disinfection and sterilization system includes a channel-type ultraviolet disinfection and sterilization device for disinfecting and sterilizing moving items, a handheld ultraviolet disinfection and sterilization device for randomly disinfecting and sterilizing relatively static items, and an ultraviolet disinfection and sterilization cabinet for disinfecting and sterilizing static items.

Referring to FIG. 5 to FIG. 8, the channel-type ultraviolet disinfection and sterilization device includes a device body 1, a conveyor 2 and a first pulsed ultraviolet disinfection and sterilization apparatus 3. Two ends of the device body 1 are respectively provided with an item inlet 11 and an item outlet 12. The item inlet 11 communicates with the item outlet 12 to form a disinfection and sterilization channel. The item inlet 11 and the item outlet 12 are respectively provided with a roller shutter door for opening or closing the disinfection and sterilization channel in one-to-one correspondence. The conveyor 2 is configured to carry and convey items such that the items are conveyed from the item inlet 11 to the item outlet 12. An inner wall of the disinfection and sterilization channel is provided with the first pulsed ultraviolet disinfection and sterilization apparatus 3 so as to disinfect and sterilize the items conveyed on the conveyor 2.

The roller shutter doors can be closed to protect the item inlet 11 and the item outlet 12. When the device needs to be opened, the roller shutter doors can be opened to expose the item inlet 11 and the item outlet 12, so that the items to be disinfected can be conveyed and disinfected, which is convenient to use.

In a specific implementation, the items to be disinfected can be placed on the conveyor 2 through the item inlet 11, and then the conveyor 2 conveys the items to be disinfected to the item outlet 12 through the disinfection and sterilization channel. During the conveying process of the items to be disinfected in the disinfection and sterilization channel, a pulsed ultraviolet irradiation apparatus may generate pulsed ultraviolet light to sterilize the items to be disinfected from all directions, so as to complete cold sterilization on the surface within a short time, thereby improving the sterilization effect. The window shades 13 arranged at the item inlet 11 and the item outlet 12 can effectively prevent the external environment from affecting the disinfection and sterilization process in the disinfection and sterilization channel. This device can disinfect and sterilize the items to be disinfected through the channel from all directions, and improve the short-time disinfection and sterilization effect on moving items. Moreover, the pulsed ultraviolet irradiation does not make the items hot, and there are no application or residues of chemicals, which is safer to use.

Figure 2:
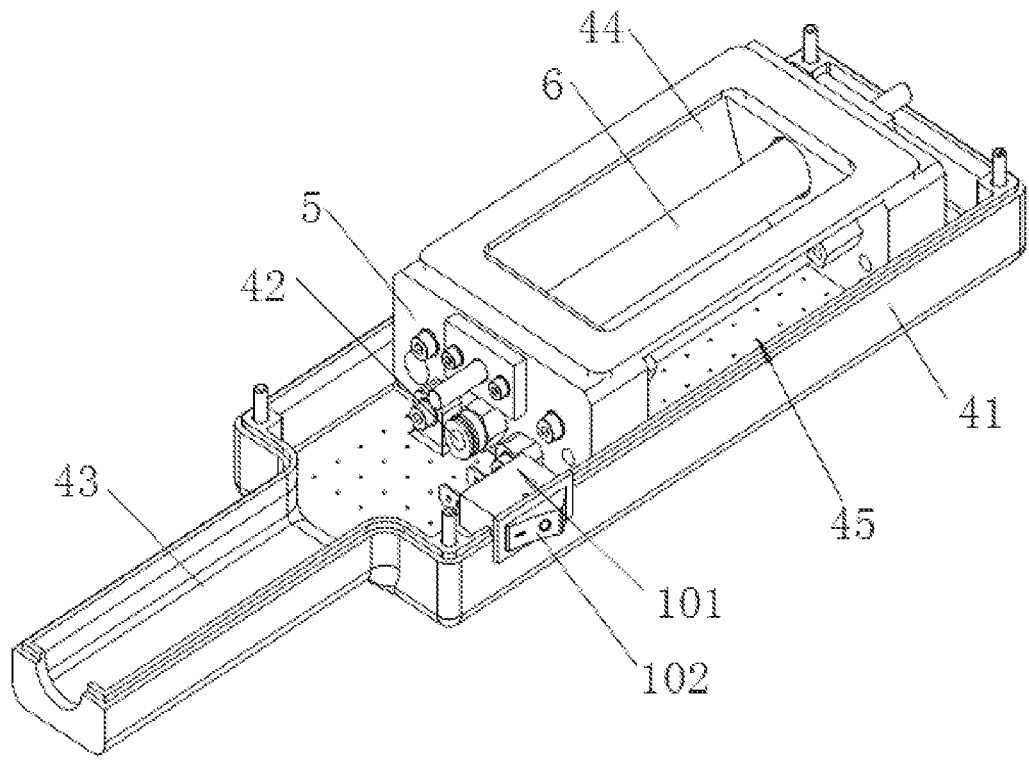
FIG. 2 is a cross-sectional view of the handheld ultraviolet disinfection and sterilization device in the high-adaptability pulsed ultraviolet disinfection and sterilization system according to an embodiment.

Referring to FIG. 1 and FIG. 2, the handheld ultraviolet disinfection and sterilization device includes a handheld shell 41, a lamp holder 5 and a second pulsed ultraviolet disinfection and sterilization apparatus 6. The second pulsed ultraviolet disinfection and sterilization apparatus 6 is connected to the handheld shell 41 through the lamp holder 5. A periphery of the handheld shell 41 is provided with a control switch 102, and an inner wall of the handheld shell 41 is provided with a single-chip microcomputer 101. One end of the single-chip microcomputer 101 is electrically connected to the second pulsed ultraviolet disinfection and sterilization apparatus 6, and the other end of the single-chip microcomputer 101 is electrically connected to the control switch 102.

In a specific implementation, the control switch 102 may send an on-off control instruction to the single-chip microcomputer 101, and the single-chip microcomputer 101 controls a pulsed ultraviolet lamp tube to emit pulsed ultraviolet light according to the instruction. The pulsed ultraviolet light emitted by the pulsed ultraviolet lamp tube is emitted to the outside of the handheld shell 41 through the disinfection and sterilization window 44. The user may hold the grip 43 by hand and align the disinfection and sterilization window 44 with the corresponding item so as to perform ultraviolet disinfection and sterilization. The user may use this handheld device to disinfect and sterilize the item by pulsed ultraviolet light, which improves the short-time disinfection and sterilization effect on the item and is more flexible and convenient to use.

The pulsed ultraviolet light is ultraviolet light that is excited using a special inert gas lamp tube in the pulse form by instantaneous discharge-based pulse engineering technology. The pulsed ultraviolet light kills various microorganisms by using the instantaneous high-intensity pulsed light energy, thereby overcoming the defects in the traditional thermal sterilization and chemical sterilization. This pulsed ultraviolet light sterilization technology is a novel cold sterilization technology that kills various microorganisms on food and packaging by using the instantaneous high-intensity pulsed light energy, and thus, has little effect on the nutritional ingredients and taste of food. Compared with the traditional sterilization methods, the pulsed ultraviolet light sterilization technology has the characteristics of short sterilization time (usually several seconds to tens of seconds), no need of direct contact with items and appliances, and controllable operations.

Figure 3:
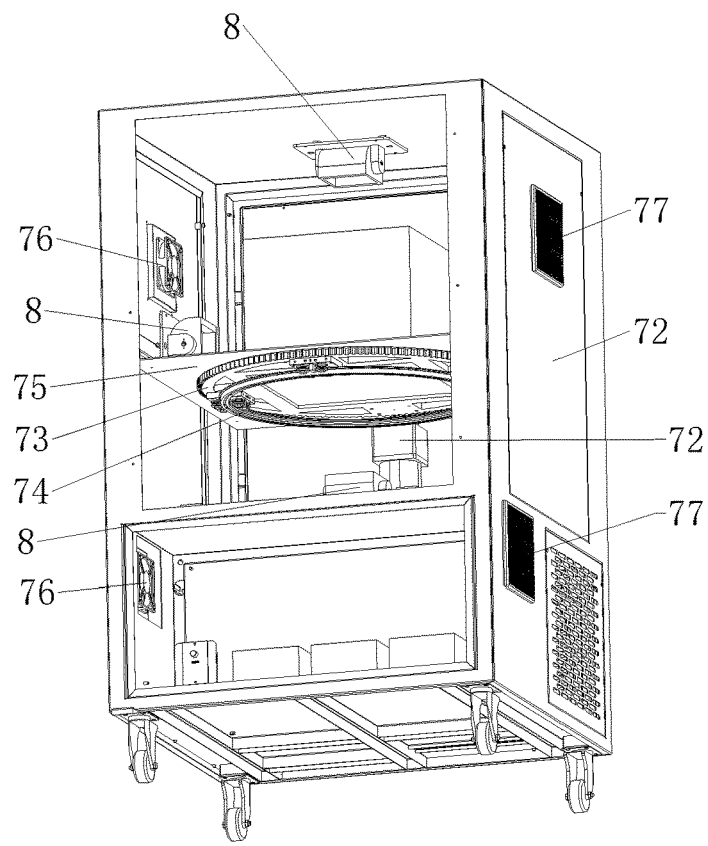
FIG. 3 is a schematic three-dimensional structural view of an ultraviolet disinfection and sterilization cabinet in the high-adaptability pulsed ultraviolet disinfection and sterilization system from a viewing angle, with part of the body removed to show the internal structure.
Figure 4:
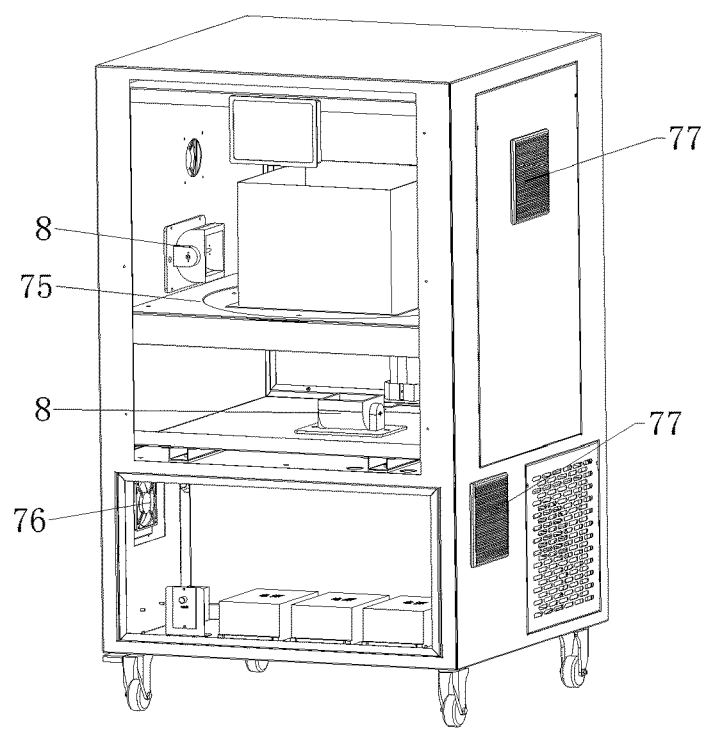
FIG. 4 is a schematic three-dimensional structural view of the ultraviolet disinfection and sterilization cabinet in the high-adaptability pulsed ultraviolet disinfection and sterilization system from another viewing angle, with part of the body removed to show the internal structure.
Figure 5:
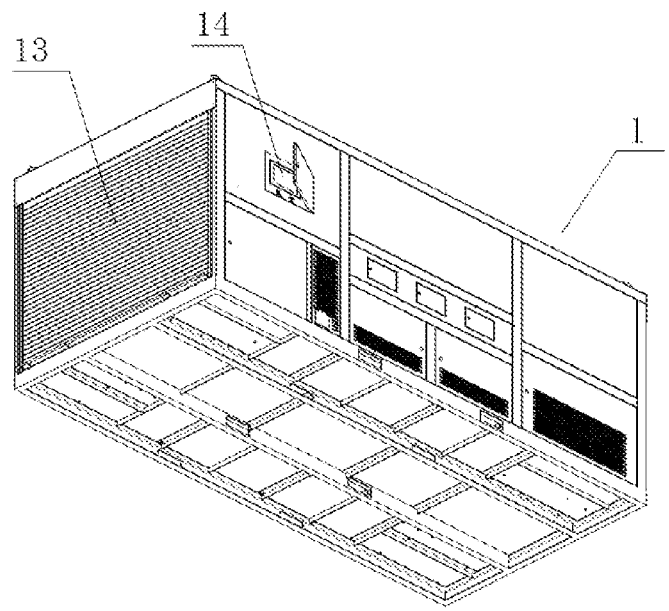
FIG. 5 is a schematic three-dimensional structural view of a channel-type ultraviolet disinfection and sterilization device in the high-adaptability pulsed ultraviolet disinfection and sterilization system according to an embodiment.
Figure 6:
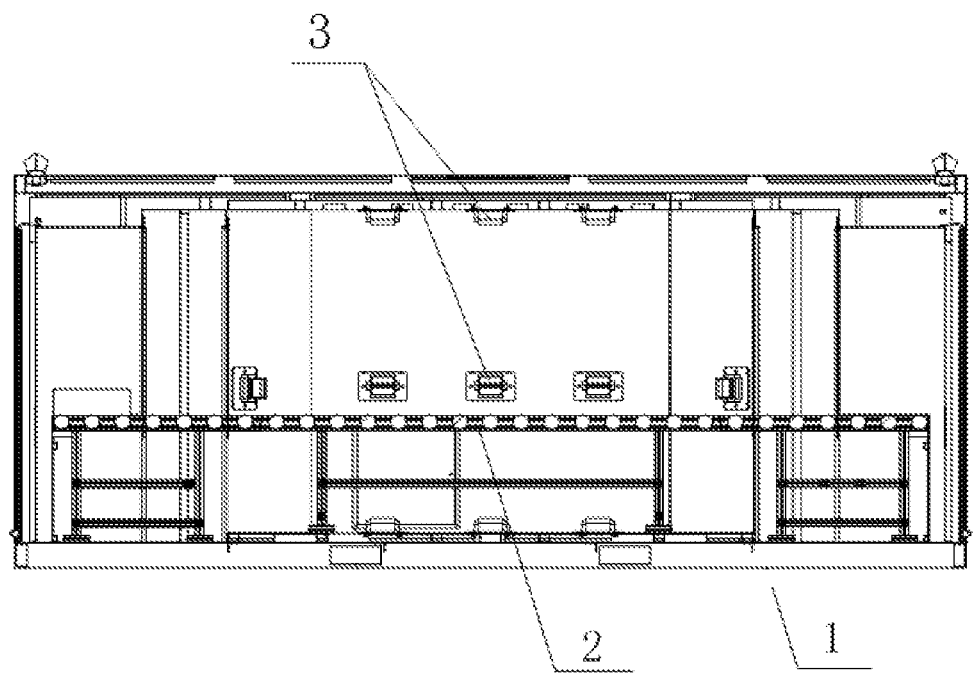
FIG. 6 is a cross-sectional view of the channel-type ultraviolet disinfection and sterilization device in the high-adaptability pulsed ultraviolet disinfection and sterilization system according to an embodiment.
Figure 7:
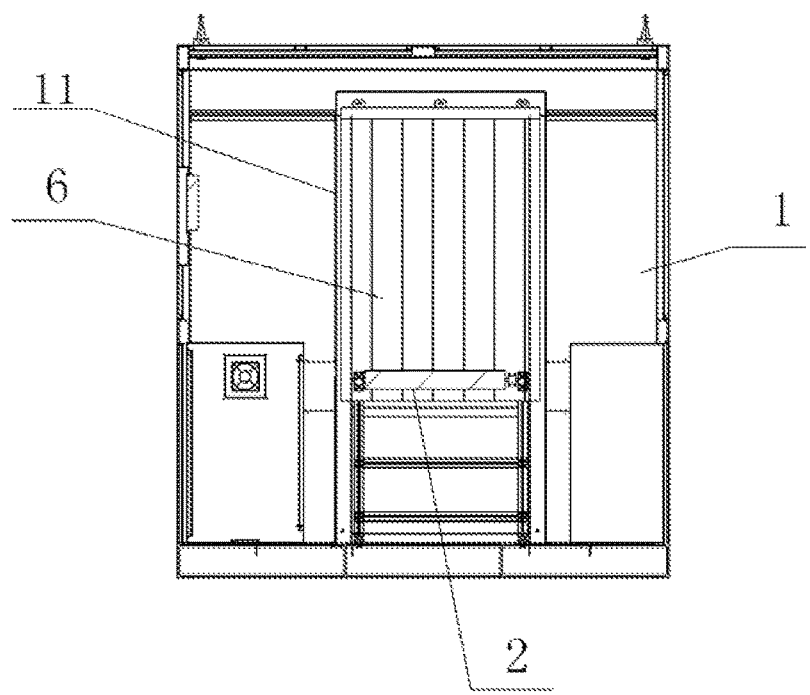
FIG. 7 is a left view of the channel-type ultraviolet disinfection and sterilization device in the high-adaptability pulsed ultraviolet disinfection and sterilization system according to an embodiment.
Figure 8:
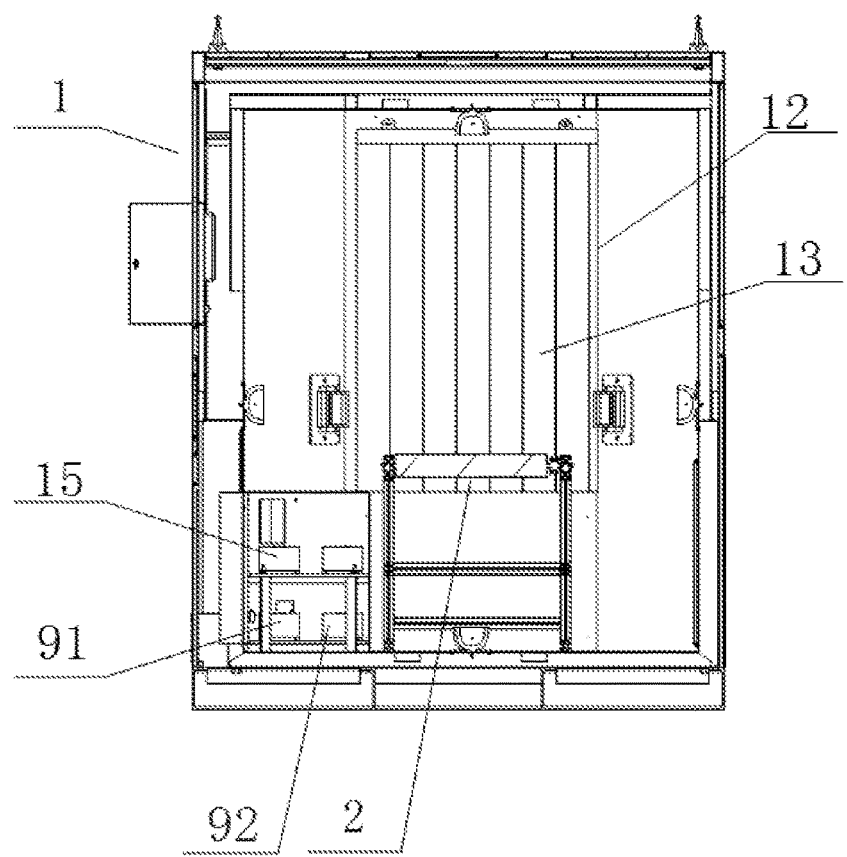
FIG. 8 is a right view of the channel-type ultraviolet disinfection and sterilization device in the high-adaptability pulsed ultraviolet disinfection and sterilization system according to an embodiment.

Referring to FIG. 3 and FIG. 4, the ultraviolet disinfection and sterilization cabinet includes a casing 71 and a third pulsed ultraviolet disinfection and sterilization apparatus 8. The casing 71 is provided with an inner cavity for accommodating items. A middle part of the inner cavity is provided with a transparent divider. A turntable 73 and a guide rail ring 74 are arranged inside the transparent divider. A transparent carrying plate 75 is embedded in the turntable 73. The transparent carrying plate 75 extends to a top surface of the transparent divider. A bottom of the transparent divider is provided with a first motor 72. The first motor 72 is configured to drive the turntable 73 to rotate on the guide rail ring 74. The third pulsed ultraviolet disinfection and sterilization apparatus 8 is connected to the casing 71 so as to disinfect and sterilize the items in the inner cavity.

The inner cavity of the casing 71 can accommodate the item to be disinfected. The item to be disinfected is placed on the transparent carrying plate 75. The turntable 73 is driven by the first motor 72 to rotate on the guide rail ring 74, thereby driving the transparent carrying plate 75 and the item to be disinfected to rotate together. The ultraviolet lamps arranged on the top, bottom and side wall of the inner cavity can uniformly and thoroughly irradiate and disinfect the upper, lower and side surfaces of the rotating item to be disinfected, which effectively improves the ultraviolet disinfection and sterilization effect on the item to be disinfected.

By means of the above technical solution, one or more of the channel-type ultraviolet disinfection and sterilization device, the handheld ultraviolet disinfection and sterilization device and the ultraviolet disinfection and sterilization cabinet can be selected according to the object to be sterilized. On the one hand, an appropriate disinfection and sterilization device can be selected according to the state of the item to disinfect and sterilize the item in all directions, such that the item can be disinfected and sterilized thoroughly. On the other hand, the energy consumption can be reduced, and the disinfection and sterilization efficiency can be improved. As a result, no matter whether the items are dynamic or static or how many items are to be disinfected and sterilized, they can be effectively disinfected and sterilized by the high-adaptability pulsed ultraviolet disinfection and sterilization system, thereby ensuring food sanitation and living sanitation and preventing bacteria from affecting human health and safety.

For example, in the epidemic situation, the handheld ultraviolet disinfection and sterilization device may be used to disinfect and sterilize keys, clothes, shoes or bags, or disinfect and sterilize a small number of items separately. The ultraviolet disinfection and sterilization cabinet can disinfect and sterilize living items such as dishes or cups to ensure food safety. In addition, in a case that there are a large number of items to be disinfected, the channel-type ultraviolet disinfection and sterilization device may be used to disinfect and sterilize the items one by one, thereby thoroughly disinfecting and sterilizing the items. Besides, the efficiency can be improved, thereby reducing the waiting time of the user.

In an embodiment provided by the disclosure, the first pulsed ultraviolet disinfection and sterilization apparatus 3, the second pulsed ultraviolet disinfection and sterilization apparatus 6 and the third pulsed ultraviolet disinfection and sterilization apparatus 8 are configured as disinfection and sterilization apparatuses having same components. The disinfection and sterilization apparatus includes a photoelectric main module, an auxiliary function options module and an automatic control module. The photoelectric main module includes a high-energy driving power supply and a pulsed xenon light source. The auxiliary function options module includes a water/air-cooling heat dissipation module, a cold light source filtering module and a photocatalytic module. The high-energy driving power supply is connected to the pulsed xenon light source through the automatic control module, and the water/air-cooling heat dissipation module, the cold light source filtering module and the photocatalytic module are all connected to the automatic control module.

Further, the pulsed xenon light source is formed by performing high-strength sealing on a high-pressure-resistant lamp tube filled with high-pressure xenon at a high temperature of 600° ° C. to 1200° C., and the automatic control module is connected to the high-energy driving power supply in a telecommunication manner so as to adjust UVC band energy excited by one pulse of the pulsed xenon light source.

The water/air-cooling heat dissipation module is configured to cool the high-energy driving power supply and the pulsed xenon light source. The water/air-cooling heat dissipation module can cool the high-energy driving power supply and the pulsed xenon light source from 100° ° C. to 25° C. within 5 s. The cold light source filtering module is configured to directionally filter high-energy ultraviolet light excited by the pulsed xenon light source to obtain UVC high-energy ultraviolet light with an wavelength of 254 nm, 265 nm or 270 nm. The photocatalytic module is filled with a catalyst therein that can catalytically convert part of ozone generated by the working pulsed xenon light source into oxygen. At an airspeed of $10000^{-1}$, the catalytic efficiency of the catalyst for 1000 ppm ozone is up to more than 99.9%.

Specifically, the photoelectric main module is configured to be capable of working stably within a temperature range of −60° C. to 60° C., and the photoelectric main module is capable of exciting ultraviolet light within a band of 200 nm to 280 nm. The photoelectric main module can work stably within the temperature range of −60° C. to 60° C., and can work continuously for more than 1000 h. The photoelectric main module has a frequency of 10 Hz, an irradiation height of 15 cm and a pulse time of 10 s, and the disinfection and sterilization efficiency for *Escherichia coli* and *Staphylococcus aureus* at −8° C. reaches more than 99.9%. When 1 KW power is input to the photoelectric main module, energies released by ultraviolet light with a wavelength of 254 nm at distances of 0.05 m, 0.2 m and 1 m are respectively 240 $W/cm^2$, 60 $W/cm^2$ and 12 $W/cm^2$, energies released by ultraviolet light with a wavelength of 265 nm at distances of 0.05 m, 0.2 m and 1 m are respectively 260 $W/cm^2$, 65 $W/cm^2$ and 13 $W/cm^2$, and energies released by ultraviolet light with a wavelength of 270 nm at distances of 0.05 m, 0.2 m and 1 m are respectively 283 $W/cm^2$, 70.75 $W/cm^2$ and 14.15 $W/cm^2$.

It can be understood that under the technical concept of the disclosure, those skilled in the art can flexibly configure the structure of the disinfection and sterilization system according to different application scenarios, and as long as the system can quickly disinfect and sterilize the items, it belongs to the technical concept of the disclosure.

In an embodiment provided by the disclosure, there are three first pulsed ultraviolet disinfection and sterilization apparatuses 3 respectively arranged on the inner wall of the disinfection and sterilization channel so as to generate pulsed ultraviolet light to disinfect and sterilize the items to be disinfected on the conveyor 2 from all directions. In this way, cold sterilization can be completed on the surface within a short time, thereby improving the sterilization effect. The window shades 13 arranged at the item inlet 11 and the item outlet 12 can effectively prevent the external environment from affecting the disinfection and sterilization process in the disinfection and sterilization channel. This device can disinfect and sterilize the items to be disinfected through the channel from all directions, and improve the short-time disinfection and sterilization effect on moving items. Moreover, the pulsed ultraviolet irradiation does not make the items hot, and there are no application or residues of chemicals, which is safer to use.

In an embodiment provided by the disclosure, a first controller 15 is arranged in the device body 1, and a periphery of the device body 1 is provided with a touch panel 14. The first controller 15 is communicatively connected to the touch panel 14, the conveyor 2 and the first pulsed ultraviolet disinfection and sterilization apparatus. A power module 92 is arranged in the device body 1, and the power module 92 is respectively electrically connected to the first controller 15, the touch panel 14, the conveyor 2 and the first pulsed ultraviolet disinfection and sterilization apparatus so as to supply power thereto. The conveyor 2 includes a support, a conveyor belt and an electric motor. The conveyor belt is mounted on the support, and the electric motor is configured to drive and control the conveyor belt to operate and communicatively connected to the first controller 15. The motor is controlled to work according to the control instruction of the first controller 15 so as to drive the conveyor belt to operate on the support, and the items to be disinfected are conveyed and disinfected in the disinfection and sterilization channel.

In a specific implementation, the power module 92 may supply working power to the apparatuses in the device body 1. The conveyor 2 and the pulsed ultraviolet irradiation apparatus may be automatically controlled by the first controller 15 to convey and disinfect the items to be disinfected. The touch panel 14 may display working states and parameters of the first controller 15, the conveyor 2 and the pulsed ultraviolet irradiation apparatus, and the user may touch the touch panel to send a corresponding touch control instruction to the first controller 15, so as to disinfect and sterilize the items.

In a possible design, a water chiller is arranged in the device body 1, and a first cooling water tube is arranged in a protective shell of the first pulsed ultraviolet disinfection and sterilization apparatus. The first cooling water tube communicates with the water chiller, and the water chiller is communicatively connected to the first controller 15. Cooling water is injected into an internal circulation of the first cooling water tube by the water chiller so as to cool and protect the first pulsed ultraviolet disinfection and sterilization apparatus. With the water chiller, the cooling water can be injected into the internal circulation of the first cooling water tube so as to cool and protect the pulsed ultraviolet irradiation apparatus, thereby ensuring the pulsed ultraviolet irradiation apparatus to work stably for a long time and preventing the disinfection and sterilization channel from becoming hot. The first controller 15 may be used to monitor and control the working state of the water chiller.

Further, a temperature sensor for detecting a temperature of water is arranged in the water chiller, and the temperature sensor is electrically connected to the first controller 15. In a specific implementation, the temperature sensor can detect the temperature of cooling water used in the internal circulation of the water chiller in real time, and transmit the detection result to the first controller 15, so as to automatically monitor the temperature of water in the water chiller. When the temperature of the cooling water is too high, the first controller 15 may give an early warning so as to prevent the pulsed ultraviolet irradiation apparatus from breakdown.

Further, an alarm is arranged in the device body 1. The alarm is electrically connected to the first controller 15. In this way, if the first controller 15 detects an operating failure in the device, it may control the alarm to give out corresponding early warning information, so that working personnel can find the current abnormalities in time.

Further, an ultraviolet sensor is arranged in the disinfection and sterilization channel. The ultraviolet sensor is electrically connected to the first controller 15. Thereby, the ultraviolet sensor may detect ultraviolet intensity in the disinfection and sterilization channel in real time and transmit the detection result to the first controller 15, so that the ultraviolet intensity in the disinfection and sterilization channel can be automatically monitored.

In a possible design, a communication module connected to the first controller 15 is further arranged in the device body 1. In a specific implementation, the first controller 15 may send operating states and parameters of the electric apparatuses in the device to an external terminal through the communication module such that corresponding personnel can check the operating states and parameters, and moreover, a remote control instruction may be received through the communication module so as to automatically control the device.

In an embodiment provided by the disclosure, a second cooling water tube 42 runs through the lamp holder 5. The grip 43 has a hollow structure inside. One end of the grip 43 is provided with a tube hole, and the second cooling water tube 42 runs through the grip 43 and extends to the outside of the grip 43 through the tube hole. An external cooling water circulation can be introduced by the aid of the second cooling water tube 42 to cool the space inside the lamp holder 5 and the handheld shell 41, thereby ensuring the single-chip microcomputer 101 and the pulsed ultraviolet lamp tube to operate stably.

In a specific design, the grip 43 has a length L=100 mm, a width h=40 mm and a height w=20 mm.

In a possible design, the handheld shell 41 is provided with a plurality of heat dissipation through holes 45. In a specific implementation, through the heat dissipation through holes 45 arranged in the handheld shell 41, the operating electric apparatus in the handheld shell 41 can be cooled by air, thereby preventing the apparatus from becoming too hot and ensuring the apparatus to operate stably.

In a possible design, the handheld shell 41 is provided with a disinfection and sterilization window 44 arranged corresponding to the second pulsed ultraviolet disinfection and sterilization apparatus 6, and the disinfection and sterilization window 44 is made of a transparent material, which can prevent mosquitoes or dust from adhering to the second pulsed ultraviolet disinfection and sterilization apparatus 6 and thus affecting the disinfection and sterilization effect.

In an embodiment provided by the disclosure, the casing 71 includes a top plate, a bottom plate, two side plates, a back cover, a door bracket, a door, four height adjusting brackets and a height adjusting plate. The top plate, the bottom plate, the two side plates, the back cover, the door bracket and the door form a casing 71 structure. The four height adjusting brackets are arranged in the casing 71 structure. The four height adjusting brackets are at equal distances from the side plates, the door and the back cover, and the height adjusting plate is arranged on the height adjusting brackets.

The third pulsed ultraviolet disinfection and sterilization apparatus 8 is mounted inside the casing 71 device. The pulsed xenon light source is mounted in the middle of the top plate of the casing 71 device. The high-energy driving power supply is mounted on the bottom plate of the casing 71 device near the side plates. The automatic control module is mounted on the side plate of the casing 71 device and located in the middle of the pulsed xenon light source and the high-energy driving power supply. The high-energy driving power supply and the pulsed xenon light source are connected to each other and to the automatic control module through high-voltage-resistant wires.

The height adjusting plate is a rectangular stainless steel plate with buckles at four corners, which are tightly fixed with the height adjusting brackets by screws. The height adjusting plate can adjust its height within a range of 0 to 400 nm. The middle of the height adjusting plate is provided with a shallow rectangular recess for mounting various molds that are used for containing various materials or items.

In a specific design, the casing 71 has a height h=600 mm, a length L=800 mm and a width w=600 mm. The door has a height h0=500 mm and a length L0=700 mm. The height adjusting brackets are located between the bottom plate and the top plate, and are respectively 50 mm from the side plates, the door and the back cover. The height adjusting plate is a rectangular stainless steel plate with buckles at four corners, which can be tightly fixed with the height adjusting brackets by screws. The height adjusting plate can adjust its height within a range of 0 to 400 nm. The middle of the height adjusting plate is provided with a shallow rectangular recess for mounting various molds that are used for containing various materials or items.

Optionally, the turntable 73 is a gear turntable 73. An output terminal of the first motor 72 is assembled with a driving gear, and the driving gear is engaged with the gear turntable 73. In a specific implementation, the first motor 72 drives the driving gear assembled to the output terminal thereof to rotate. Since the driving gear is engaged with the gear turntable 73, the turntable 73 is further driven to rotate, so that the transparent carrying plate 75 and the item to be disinfected are driven to rotate together and uniformly irradiated by ultraviolet light.

Furthermore, the bottom of the casing 71 is provided with casters. In a specific implementation, the bottom of the casing 71 is provided with casters, so that the casing 71 can be moved conveniently.

In an embodiment, the side wall of the inner cavity of the casing 71 and the side surface of the ultraviolet lamp power supply are respectively provided with a heat dissipation fan 76. In a specific implementation, the side wall of the inner cavity and the side surface of the ultraviolet lamp power supply are respectively provided with the heat dissipation fan 76, so that the ultraviolet lamps and the ultraviolet lamp power supply can be cooled by air efficiently, which prevents the ultraviolet lamps and the ultraviolet lamp power supply from becoming hot and damaged during the working process, and ensures the ultraviolet lamps and the ultraviolet lamp power supply to work continuously.

Furthermore, the casing 71 is provided with heat dissipation shutters 77 respectively facing the heat dissipation fans 76. In a specific implementation, the casing 71 is provided with the heat dissipation shutters 77 respectively facing the heat dissipation fans 76, so that the heat dissipation fans 76 can smoothly expel hot air to the outside of the casing 71 through the heat dissipation shutters 77, thereby achieving efficient cooling.

Furthermore, a second water chiller is arranged inside the casing 71 near the ultraviolet lamp power supply. In a specific implementation, the second water chiller is arranged inside the casing 71 near the ultraviolet lamp power supply, which can further achieve cooling with water and thus improve the cooling effect on the ultraviolet lamp power supply.

One side of the casing 71 is provided with the door facing the inner cavity. The door is provided with a touch screen and an electronic lock. A controller is arranged in the door. The controller is electrically connected to the ultraviolet lamp power supply, the first motor 72, the touch screen and the electronic lock. In a specific implementation, the controller may be controlled through the touch screen to open the electronic lock so as to open the door, and the item to be disinfected may be put into the casing. Then, the door may be closed, and the electronic lock is closed automatically. After that, the controller may be controlled through the touch screen to turn on the ultraviolet lamps and the first motor 72 to disinfect and sterilize the item to be disinfected by means of ultraviolet light.

The preferred implementations of the disclosure have been described in detail above in conjunction with the accompanying drawings, but the disclosure is not limited to the specific details in the above implementations, and various simple variations may be made to the technical solutions of the disclosure within the scope of the technical idea of the disclosure. These simple variations are all within the scope of the disclosure.

What is claimed is:

1. A high-adaptability pulsed ultraviolet disinfection and sterilization system, comprising a channel-type ultraviolet disinfection and sterilization device for disinfecting and sterilizing moving items, a handheld ultraviolet disinfection and sterilization device for randomly disinfecting and sterilizing relatively static items, and an ultraviolet disinfection and sterilization cabinet for disinfecting and sterilizing static items;

wherein the channel-type ultraviolet disinfection and sterilization device comprises a device body (1), a conveyor (2) and a first pulsed ultraviolet disinfection and sterilization apparatus (3); two ends of the device body (1) are respectively provided with an item inlet (11) and an item outlet (12), the item inlet (11) communicating with the item outlet (12) to form a disinfection and sterilization channel; the item inlet (11) and the item outlet (12) are respectively provided with a roller shutter door for opening or closing the disinfection and sterilization channel in one-to-one correspondence; the conveyor (2) is configured to carry and convey items such that the items are conveyed from the item inlet (11) to the item outlet (12); an inner wall of the disinfection and sterilization channel is provided with the first pulsed ultraviolet disinfection and sterilization apparatus (3) so as to disinfect and sterilize the items conveyed on the conveyor (2);

the handheld ultraviolet disinfection and sterilization device comprises a handheld shell (41), a lamp holder (5) and a second pulsed ultraviolet disinfection and sterilization apparatus (6), the second pulsed ultraviolet disinfection and sterilization apparatus (6) being connected to the handheld shell (41) through the lamp holder (5); a periphery of the handheld shell (41) is provided with a control switch (102), and an inner wall of the handheld shell (41) is provided with a single-chip microcomputer (101), one end of the single-chip microcomputer (101) being electrically connected to the second pulsed ultraviolet disinfection and sterilization apparatus (6), and the other end of the single-chip microcomputer (101) being electrically connected to the control switch (102);

the ultraviolet disinfection and sterilization cabinet comprises a casing (71) and a third pulsed ultraviolet disinfection and sterilization apparatus (8), the casing (71) being provided with an inner cavity for accommodating items, a middle part of the inner cavity being provided with a transparent divider, a turntable (73) and a guide rail ring (74) being arranged inside the transparent divider, a transparent carrying plate (75) being embedded in the turntable (73), the transparent carrying plate (75) extending to a top surface of the transparent divider, a bottom of the transparent divider being provided with a first motor (72), and the first motor (72)

being configured to drive the turntable (73) to rotate on the guide rail ring (74); and the third pulsed ultraviolet disinfection and sterilization apparatus (8) is connected to the casing (71) so as to disinfect and sterilize the items in the inner cavity.

2. The high-adaptability pulsed ultraviolet disinfection and sterilization system according to claim 1, wherein the first pulsed ultraviolet disinfection and sterilization apparatus (3), the second pulsed ultraviolet disinfection and sterilization apparatus (6) and the third pulsed ultraviolet disinfection and sterilization apparatus (8) are configured as disinfection and sterilization apparatuses having same components, the disinfection and sterilization apparatus comprising a photoelectric main module, an auxiliary function options module and an automatic control module;

wherein the photoelectric main module comprises a high-energy driving power supply and a pulsed xenon light source; the auxiliary function options module comprises a water/air-cooling heat dissipation module, a cold light source filtering module and a photocatalytic module; and the high-energy driving power supply is connected to the pulsed xenon light source through the automatic control module, and the water/air-cooling heat dissipation module, the cold light source filtering module and the photocatalytic module are all connected to the automatic control module.

3. The high-adaptability pulsed ultraviolet disinfection and sterilization system according to claim 2, wherein the pulsed xenon light source is formed by performing high-strength sealing on a high-pressure-resistant lamp tube filled with high-pressure xenon at a high temperature of 600° C. to 1200° C., and the automatic control module is connected to the high-energy driving power supply in a telecommunication manner so as to adjust UVC band energy excited by one pulse of the pulsed xenon light source.

4. The high-adaptability pulsed ultraviolet disinfection and sterilization system according to claim 2, wherein the photoelectric main module is configured to be capable of working stably within a temperature range of −60° C. to 60° C., and the photoelectric main module is capable of exciting ultraviolet light within a band of 200 nm to 280 nm.

5. The high-adaptability pulsed ultraviolet disinfection and sterilization system according to claim 1, wherein there are three first pulsed ultraviolet disinfection and sterilization apparatuses (3) respectively arranged on the inner wall of the disinfection and sterilization channel so as to generate pulsed ultraviolet light to disinfect and sterilize the items to be disinfected on the conveyor (2) from all directions.

6. The high-adaptability pulsed ultraviolet disinfection and sterilization system according to claim 1, wherein a first controller (15) is arranged in the device body (1), and a periphery of the device body (1) is provided with a touch panel (14); the first controller (15) is communicatively connected to the touch panel (14), the conveyor (2) and the first pulsed ultraviolet disinfection and sterilization apparatus (3);

a power module (92) is arranged in the device body (1), and the power module (92) is respectively electrically connected to the first controller (15), the touch panel (14), the conveyor (2) and the first pulsed ultraviolet disinfection and sterilization apparatus (3) so as to supply power thereto; and the conveyor (2) comprises a support, a conveyor belt and an electric motor, the conveyor belt being mounted on the support, and the electric motor being configured to drive and control the conveyor belt to operate and communicatively connected to the first controller (15).

7. The high-adaptability pulsed ultraviolet disinfection and sterilization system according to claim 6, wherein a water chiller is arranged in the device body (1), and a first cooling water tube is arranged in a protective shell of the first pulsed ultraviolet disinfection and sterilization apparatus, the first cooling water tube communicating with the water chiller, and the water chiller being communicatively connected to the first controller (15); cooling water is injected into an internal circulation of the first cooling water tube by the water chiller so as to cool and protect the first pulsed ultraviolet disinfection and sterilization apparatus; and a temperature sensor for detecting a temperature of water is arranged in the water chiller, and the temperature sensor is electrically connected to the first controller (15).

8. The high-adaptability pulsed ultraviolet disinfection and sterilization system according to claim 6, wherein an alarm is arranged in the device body (1), the alarm being electrically connected to the first controller (15); and an ultraviolet sensor is arranged in the disinfection and sterilization channel, the ultraviolet sensor being electrically connected to the first controller (15).

9. The high-adaptability pulsed ultraviolet disinfection and sterilization system according to claim 1, wherein a second cooling water tube (42) runs through the lamp holder (5), and the handheld shell (41) is provided with a grip (43), the grip (43) having a hollow structure inside, the grip (43) being provided with a tube hole, and the second cooling water tube (42) running through the grip (43) and extending to a water tank outside the grip (43) through the tube hole.

10. The high-adaptability pulsed ultraviolet disinfection and sterilization system according to claim 1, wherein the handheld shell (41) is provided with a disinfection and sterilization window (44) arranged corresponding to the second pulsed ultraviolet disinfection and sterilization apparatus (6), and the disinfection and sterilization window (44) is made of a transparent material.

* * * * *